United States Patent [19]

Suga

[11] Patent Number: 4,699,930
[45] Date of Patent: Oct. 13, 1987

[54] COSMETIC COMPOSITION

[76] Inventor: Kazuo Suga, No. 30-2, 3-chome, Higashi-ogu, Arakawa-ku, Tokyo, Japan

[21] Appl. No.: 765,570

[22] Filed: Aug. 14, 1985

Related U.S. Application Data

[63] Continuation of Ser. No. 445,516, Nov. 30, 1982, abandoned.

[30] Foreign Application Priority Data

Oct. 12, 1982 [JP] Japan ............................ 57-178904

[51] Int. Cl.$^4$ ................................................ A61K 7/48
[52] U.S. Cl. ...................................... 514/25; 514/846; 514/847; 514/886; 514/887; 514/937; 514/844
[58] Field of Search .......................................... 514/844

[56] References Cited

U.S. PATENT DOCUMENTS

| 4,130,667 | 12/1978 | Smith | 424/361 |
| 4,151,304 | 4/1979 | Evans | 424/361 |

FOREIGN PATENT DOCUMENTS

| 1467871 | 1/1969 | Fed. Rep. of Germany | 424/180 |
| 2154277 | 5/1972 | Fed. Rep. of Germany | 424/180 |
| 2757937 | 6/1979 | Fed. Rep. of Germany | 424/101 |
| 4823908 | 7/1973 | Japan | 424/101 |
| 0147213 | 11/1980 | Japan | 424/101 |
| 0088107 | 6/1982 | Japan | 424/101 |

OTHER PUBLICATIONS

The Potential for Industrial Uses of Sucrose, by Hickson, in Sugar: Science and Technology, pp. 158–171, 1979.

Gas Chromatographic Differentation of 4–desmethyl, 4–monomethyl and 4,4–dimethylsterols, by Itoh et al., in steroids, vol. 23, No. 5, pp. 668–698, May 1974.

Reaction of Sodium Sucrate in Solution, by Reeder et al., in I & EC Product Research Development, pp. 230–234, Dec. 1968.

The Effect of Topically Applied γ-Oryzanol on Sebaceous Glands by Ueda et al., in the Journal of Dermatology, vol. 3, No. 1, pp. 19–24, Feb. 1976.

Chem. Abs., 1969, vol. 70, pp. 106716y, Tachibana.
Chem. Abs., 1979, vol. 91, pp. 39729y, Tsuchiga.

*Primary Examiner*—Dale R. Ore
*Attorney, Agent, or Firm*—Armstrong, Nikaido, Marmelstein & Kubovcik

[57] ABSTRACT

The present invention is a cosmetic composition that raffinose ester of higher fatty acid having carbon atoms from 14 to 20 and cane sugar fatty acid ester are used in parallel, further solcoseryl is compounded to the above. The composition according to the present invention are stable and do not give the irritation on the skin, has no variable nature and has an excellent moisture retaining ability, and then can give the cosmetics which the feeling obtained by employing said cosmetics is very satisfactory. Further the solcoseryl that the substance which deoxyribonucleic acid is dissolved in the raffinose ester of higher fatty acid is added under the sterile condition can be compounded in this cosmetic composition.

6 Claims, No Drawings

COSMETIC COMPOSITION

This application is a continuation of application Ser. No. 445,516 filed Nov. 30, 1982 now abandoned.

BRIEF SUMMARY OF THE INVENTION

The present invention relates to a stable cosmetic composition over wide range of pH, characterized in that raffinose ester of higher fatty acid and cane sugar fatty acid ester are used jointly, further solcoseryl is compounded to the above, and a variable nature is lack, a skin irritation is not given, and also a surpassing utility feeling which a moist feeling is given with the skin after using said cosmetic composition by superior moisture retaining ability of solcoseryl is in existance.

Normally, cosidering an emsulsifying agent and a dispersing agent which are used in cosmetic cream and milky lotion and the like, cation active agent such as quaternary ammonium, anion active agent such as alkali salt of fatty acid and sulfuric ester of higher alchol, or amphoteric active agent such as lecithin, or sorbitan fatty acid ester and polyoxyethylene, nonionic active agent such as higher alcohol ether are applied individually or by combined employment, but it is necessary that considering an emulsifying agent and a dispersing agent, lipophilic group and hydrophilic group are retained with an adequate rate, functions which make oil in water or water in oil emulsify, dissolve or disperse sufficiently in compliance with kind of cosmetics are in existence, concurrently functions which maintain cosmetics in long stable state without damage from agricultural chemicals on human body are in existence.

In the combined employment of raffinose ester of higher fatty acid and cane sugar fatty acid ester used in the present invention, the above esters have no poisonous properties, together, also hydrophilic group and lipophlic group are retained with adequate rate, and surpassing functions which make oil in water and water in oil emulsify, dissolve or disperse sufficiently are in existance and then stable homogenous products can be produced.

Also, solcoseryl has surpassing moisture retaining ability and hygroscopic ability, and the products of cosmetic composition which this solcoseryl is compounded have superior effects in regard to "moisture feeling on the skin after using said product", "smoothness on the skin" or "cosmetic spread" and the like.

Namely, it is not too much to say that quality of utility feeling of the cosmetics depends on quality of the moisture retaining ability of said cosmetics.

When the substance which DNA is dissolved in the raffinose ester of higher fatty acid is added to solcoseryl, further the elevation from 30 to 60% in this moisture retaining ability is obtained.

It is recognized that in respect of the cosmetics in the cosmetics composition of the present invention which the above substance are compounded, a primary irritative property of the skin is not recognized in the animal test including cream, pack, milky lotion and beauty wash employed, and also DNA injuring property is not in existance in the result of restorative test using a microorganism which is carried out as the screening test for research of carcinogenic substances.

The raffinose used in the present invention is included in sugar beet and cotton seed, and also said raffinose is a trisaccaride being included in the waste fluid of Stephen reaction on the occasion of collecting cane sugar, the chemical structure of raffinose is as follows:

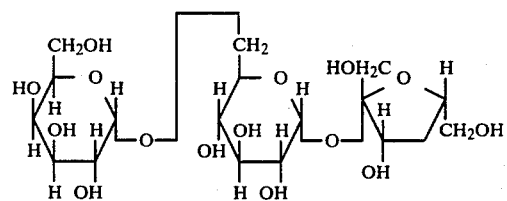

That is to say, this raffinose is one kind of trisaccaride, and consists of one molecular each of D-galactose, D-glucose and D-fructose. The structure corresponds to the substance which D-galacto-pyranose carried out α-glucoside connection on carbon atom of sixth place within chemical structure of D-glucose in the molecule of cane sugar.

Raffinose ester RAFFI-140 which is used in examples of the composition of the present invention is higher saturated fatty acid ester which is composed of raffinose and myristic acid principally, and when this dried article is quantified, myristic acid raffinose above 90% is included, molecular number of myristic acid connected with one molecule of raffinose is in the range from 1.0 to 1.6.

Also, RAFFI-180 is higher saturated fatty acid ester which is composed of raffinose and stearic acid principally, and when this dried article is quantified, stearic acid raffinose above 90% is included, molecular number of stearic acid connected with one molecule of raffinose is in the range from 1.0 to 1.6.

Cane sugar fatty acid ester used in the cosmetic composition of the present invention, is the product having the quality established in accordance with the cosmetic quality standard.

Also, solcoseryl used in the cosmetic composition of the present invention is the substance which is imported from Solcovarsel Co., Ltd, in Swiss, and reticuloendothelium of young cattle in the golden age is invigorated, whole blood of said cattle is collected and a preliminary operation for extraction is carried out, and then the extraction is performed, protein, pyrogen and antigenicity substance are removed and concentration is carried out, therefore said solcoseryl is manufactured, and further said solcoseryl is the substance that methylparaben of 0.18% and propylparaben of 0.02% are added as a preserving agent. This article is a light brown transparent liquid.

This article is already imported and approved as medical supplies, and is utilized on the granulation plastic promoting medical treatments in external injury, burn and operative injury, but also said article has very excellent moisture retaining ability and hygroscopic ability as mentioned above.

The deoxyribonucleic acid (DNA) is the substance which is obtained from the thymus of calves or the spermary of fish, and deoxyribonucleotide becomes an unit, this DNA is polynucleotide of macromolecule which said deoxyribouncleotide is polymerized by phosphoric group, and the properties are almost water insoluble white or analogical white powder.

RAFFIPENET-010 is the substance that is added to the solcoseryl by dissolving DNA compounded in the composition of the present invention in the raffinose ester, this substance has the composition as indicated next.

| RAFFIPENET-010 | |
|---|---|
| solcoseryl | 1,000 ml |
| RAFFI-010 | 50 ml |
| | 1,050 ml |

The above substances are added under sterile condition and are stirred uniformly. Also RAFFI-010 is a colorless transparent aqueous solution which is composed of DNA and RAFFI-180.

DETAILED DESCRIPTION OF THE INVENTION

When the above present invention is carried out, the aforesaid raffinose ester, cane sugar fatty acid ester and solcoseryl or RAFFIPENET-010 are mixed with raw materials, auxiliary agents, additives and the like, and therefore the skin's cosmetics including cream, milky lotion, pack, lotion and the like are obtained.

It is desirable that the contents of raffinose ester and cane sugar fatty acid ester are form 2 to 4 parts in the case of cream and milky lotion, from 0.5 to 1 parts in the case of pack and from 0.1 to 0.2 parts in the case of beauty wash, and also the contents of solcoceryl or RAFFIPENET-010 are three parts in the case of cream and milky lotion, 5 parts in the case of pack, and 3 parts in the case of beauty wash.

EXAMPLE 1

Cream

| | | weight % |
|---|---|---|
| A | cetanol | 2.5 |
| | spermaceti | 2.0 |
| | squalene | 8.0 |
| | octyldodecanol | 5.0 |
| | lanolin | 1.0 |
| | avocado oil | 1.0 |
| | stearic acid | 2.0 |
| | acetic acid-dl-α-tocophenol | 0.2 |
| | cane sugar fatty acid ester | 3.5 |
| | paraoxybutylbenzoate | 0.1 |
| | paraoxypropylbenzoate | 0.05 |
| | mica titanium | 0.25 |
| B | refined water | 62.09 |
| | concentrated glycerin | 5.0 |
| | paraoxymethybenzoate | 0.1 |
| | cholhexidine gluconate solution (20% aqueous solution) | 0.2 |
| | hinokitiol | 0.03 |
| | RAFFI-140 | 1.6 |
| | RAFFI-180 | 2.0 |
| C | solcoseryl | 3.0 |
| | blue NO. 1 | 0.08 |
| D | ready mixed perfume | 0.3 |
| | | 100.0 |

(A) is heated at 80° C., stirred and mixed. In addition, the substance which (B) is heated at 85° C. and dissolved is added to the former, this is maintained at 80° C. for 30 minutes and is cooled gradually with stirring, and then (C) is added to the above at 60° C. Further, (D) is added to the above substance at 50° C., is stirred and cooled up to 30° C., after standing for one day and night this article is filled up in the container and is wrapped, and the product is obtained.

EXAMPLE 2

Milky lotion

| | | weight % |
|---|---|---|
| A | squalene | 2.0 |
| | octyldodecanol | 2.0 |
| | stearic acid | 5.0 |
| | cetanol | 1.2 |
| | spermacetic | 2.0 |
| | cetyllactate | 0.5 |
| | cane sugar fatty acid ester | 3.0 |
| | avocado oil | 1.0 |
| | paraoxybutylbenzoate | 0.1 |
| | paraoxypropylbenzoate | 0.05 |
| B | refined water | 70.5 |
| | concentrated glycerin | 5.0 |
| | paraoxymethylbenzoate | 0.1 |
| | chlorhexicidine gluconate solution (20% aqueous solution) | 0.2 |
| | hinokitiol | 0.03 |
| | RAFFI-140 | 1.8 |
| | RAFFI-180 | 2.1 |
| C | RAFFIPENET-010 | 3.0 |
| | blue NO. 1 (0.1% aqueous solution) | 0.12 |
| D | ready mixed perfume | 0.3 |
| | | 100.0 |

(A) is heated at 80° C., stirred and mixed. In addition, the substance which (B) is heated at 85° C. and dissolved is added to the former, after the above is stirred for 30 minutes while the above is maintained at 80° C., the above is cooled gradually with stirring, and (C) is added to the above at 60° C., further (D) is added to this above substance at 50° C., stirred and cooled up to 30° C., and after standing for one day and night, then this article is filled up in the container and wrapped, and the product is obtained.

EXAMPLE 3

Pack

| | weight % |
|---|---|
| 1. stearic acid | 0.53 |
| 2. triethanolamine | 0.03 |
| 3. refined water | 67.13 |
| 4. cane sugar fatty acid ester | 1.0 |
| 5. RAFFI-140 | 0.8 |
| 6. hinokitiol | 0.03 |
| 7. concentrated glycerin | 2.0 |
| 8. allantoin | 0.1 |
| 9. paraoxymethylbenzoate | 0.1 |
| 10. chlorhexidine gluconate solution | 0.25 |
| 11. polyvinylalcohol | 19.0 |
| 12. naturon 2 × IPA | 0.5 |
| 13. ethanol | 3.3 |
| 14. ready mixed perfume | 0.15 |
| 15. solcoseryl | 5.0 |
| 16. blue NO. 1 (0.1% aqueous solution) | 0.08 |
| | 100.0 |

(a) 1 is heated at 80° C. In addition, 2 and a part of 3 are heated at 85° C., and this is added to the former, stirred and mixed, and then is cooled up to 25° C.

(b) 4 and 5 are warmed at 60° C., 6 is added to this, stirred and mixed, and further 7, 8, 9 and 10 are added to the above and stirred, and this substance is added to the residual quantity of 3, stirred and mixed. Then 11 is added to this liquid gradually, heated up to 80° C., stirred and dissolved, and is cooled up to 60° C.

Subsequently, (a) and 12 are added to liquid (b), stirred and cooled up to 30° C., and the mixed liquid of 13 and 14 is added to the above, and further 15 and 16 are added to this above with stirring, the substance which this above material is filtered with filter cloth is filled up in the container and wrapped, and then the product is obtained.

EXAMPLE 4
Lotion

|   | weight % |
|---|---|
| 1. RAFFI-140 | 0.1 |
| 2. RAFFI-180 | 0.05 |
| 3. cane sugar fatty acid ester | 0.1 |
| 4. allantion | 0.1 |
| 5. ethanol | 3.0 |
| 6. concentrated glycerin | 3.0 |
| 7. paraoxymethylbenzoate | 0.1 |
| 8. paraoxyethylbenzoate | 0.05 |
| 9. chlorhexidine gulconate solution (20% aqueous solution) | 0.25 |
| 10. hinokitiol | 0.03 |
| 11. RAFFIPENET-010 | 3.0 |
| 12. refined water | 89.96 |
| 13. ready mixed perfume | 0.2 |
| 14. blue No. 1 (0.1% aqueous solution) | 0.05 |
| 15. yellow No. 4 (0.1% aqueous solution) | 0.01 |
|   | 100.0 |

13 is kneaded together with fiber cellulose, 12 is put in the above, and stirred for 30 minutes, subsequently filtered. 1, 2, 3, 4, 6, 7, 8, 9 and 10 are added to this filtrate, warmed at 60° C., stirred and dissolves, and subsequently are cooled up to 30° C. Further, 5 and 11 are added to this above liquid, stirred and mixed, and finally 14 and 15 are added to the above, stirred and mixed, and the substance which this above material is filtered with filter cloth is easily filled up in the container, wrapped, and then the product is obtained.

Further, in respect of the raw materials used in the examples, the substances which are in conformity with the quality standard of cosmetics are used, but the qualities of used raw materials which are not indicated in the Table of quality standard are as follows:

(i) Avocado oil

This oil is an oil and fat collected from fruits of alligator pear said oil is a transparent oily liquid showing from light yellow color, and an odor and a taste of this oil exhibit peculiarities.

| refractive index | $N_D^{20}$ | 1.467–1.474 |
|---|---|---|
| specific gravity | $D_{20}^{20}$ | 0.914–0.921 |

(manufactured by Kishimoto special cod-liver oil industrial Co., Ltd).

(ii) Naturon 2XIPA

This article is a mixture which collected and refined scale glutinant of herring is dispersed in the isopropanol.

| content ratio: scale-foil | 22% (weight %) |
|---|---|
| cosmetic rudiment: isopropanol | 78% |

This properties are dispersed liquid having pearly gloss, and this article has peculiar odor.

(manufactured by Rona Pearl Co., Ltd. (USA)).

It was confirmed that the test for the products of the present invention manufactured as above-mentioned is carried out on animal and a irritative property is lack nearly in this products.

(1) Primary irritative test for skin experimental material and experimental method 1-1. Experimental object The experimental objects are product's group which are compounded with RAFFI-140, RAFFI-180, cane sugar fatty acid ester and solcoseryl or RAFFIPENET-010, that is, cream, pack, milky lotion and beauty wash products. Compounding in the products is according to the examples respectively, and compounding quantities of RAFFI-140, RAFFI-180, cane sugar fatty acid ester and solcoseryl or RAFFIPENET-010 are as follows:

|   | RAFFI-140 | RAFFI-180 | cane sugar fatty acid ester | solcoseryl or RAFFI-PENET-010 |
|---|---|---|---|---|
| cream | 1.6 | 2.0 | 3.5 | 3 |
| milky lotion | 1.8 | 2.1 | 3.0 | 3 |
| pack | 0.8 |   | 1.0 | 5 |
| beauty wash | 0.1 | 0.05 | 0.1 | 3 |

1-2. Experimental animals

The total twelve heads of female guinea pig with the weight from 340 to 420 g (average weight 385 g) in Hartley's group are used for the experiment at the rate of three heads per one product. The applying regions of the experimental object are set up in total six places by preparing three places each on left or right sides respectively of the spinal central line per one head, and three places on right side are chosen on the healthy skin, three places on left side are chosen on horny layer exfoliating skin. The hairs on both healthy skin and horny layer exfoliating skin are cut by electric razor, after cutting hairs by electric hair clippers before 24 hours for the time which the experimental objects are applied.

After the hairs on horny layer exfoliating skin are cut, this was used by exfoliating horny layer with cellophane tape.

1-3. Experimental method

The quantity of 0.1 g per respective experimental objects including cream, milky lotion and pack and the volume of 0.05 ml for beauty wash are applied on each part of cloth in miniature size of adhesive plaster for batch test (manufactured by Torii medicines Co., Ltd), they were applied on the upper back's skin of guinea pig for 24 hours. The adhesive plasters for batch test were removed after application amounting to 24 hours.

1-4. Method for judging

The adhesive plasters for batch test were removed after application amounting to 24 hours, and the skins were observed after 4, 24 and 48 hours in the removal respectively.

| deep red dapples are lacking | — |
|---|---|
| very slight deep red dapples are found (narrowly recognized degree) | ± |
| obvious deep red dapples are found | + |
| deep red dapples accompanied by edema are found | ++ |
| deep red dapples accompanied by eruption are found | +++ |

|   | healthy skin hours | | | horny layer exfoliating skin hours | | |
|---|---|---|---|---|---|---|
| judgment | 4 | 24 | 48 | 4 | 24 | 48 |

1-4-1 Cream

|       |   |   |   |   |   |   |
|-------|---|---|---|---|---|---|
| −     | 3 | 3 | 3 | 3 | 3 | 3 |
| ±     |   |   |   |   |   |   |
| +     |   |   |   |   |   |   |
| ++    |   |   |   |   |   |   |
| +++   |   |   |   |   |   |   |

1-4-2 Milky lotion

|       |   |   |   |   |   |   |
|-------|---|---|---|---|---|---|
| −     | 3 | 3 | 3 | 1 | 3 | 3 |
| ±     |   |   |   | 2 |   |   |
| +     |   |   |   |   |   |   |
| ++    |   |   |   |   |   |   |
| +++   |   |   |   |   |   |   |

1-4-3 Pack

|       |   |   |   |   |   |   |
|-------|---|---|---|---|---|---|
| −     |   | 2 | 3 | 3 | 2 | 3 | 3 |
| ±     |   | 1 |   |   | 1 |   |   |
| +     |   |   |   |   |   |   |   |
| ++    |   |   |   |   |   |   |   |
| +++   |   |   |   |   |   |   |   |

1-4-4 Beauty wash

|       |   |   |   |   |   |   |
|-------|---|---|---|---|---|---|
| −     | 3 | 3 | 3 | 2 | 3 | 3 |
| ±     |   |   |   | 1 |   |   |
| +     |   |   |   |   |   |   |
| ++    |   |   |   |   |   |   |
| +++   |   |   |   |   |   |   |

1-4-5. Conclusion

It is consideren that primary irritations on healty skin and horny layer exfoliating skin do not exsit in respective cosmetic products including cream, pack and milky lotion.

(2) Poisonous test by light

The experimental objects similar to the matters used in the primary irritative test for skin of (1) are prepared, the adhesive plasters for batch test are removed after application amounting to 24 hours, and six lights of FL-20-BLB lamp are used in parallel on all animals, then these lights were irradiated for 40 minutes at distance of 7.5 cm from a source of light.

Subsequently, three lights of FL-20-SB and three lights of FL-20-SD are juxtaposed alternatively, and these lights were irradiated for 40 minutes at distance of 7.5 cm from a source of light.

The regions of wave length and the luminous intensity of radiation of the lamps used are as follows:

2-1. The regions of wave length (a) FL-20-BLB (manufactured by Tokyo Shibaura Electrical Co., Ltd.) width of wave length 330–430 nm, peak of wave length 360 nm 20 W.

(b) FL-20-SB (manufactured by Tokyo Shibaura Electrical Co., Ltd.) width of wave length 310–610 nm, peak of wave length 400 nm 20 W.

(c) FL-20-SD (manufactured by Tokyo Shibaura Electrical Co., Ltd.) width of wave length 360–700 nm, peak of wave length 480 nm 570 nm 20 W.

2-2. The luminous intensity of radiation (measured by using the intensity meter of ultraviolet rays UVR-365 manufactured by Topcon.)

(a) Six lights of FL-20-BLB lamp are used in parallel, and the luminous intensity of radiation which is measured on the occasion of distance of 7.5 cm from a source of light is 5400 $\mu$W/cm/sec.

(b) Three lights of FL-20-SB lamp and three lights of FL-20-SD lamp are used in parallel alternatively, and the luminous intensity of radiation which is measured at distance of 7.5 cm from a source of light is 800 $\mu$W/cm/sec.

On the occasion of irradiation three heads of guinea pig are placed in the metallic basket, and the position of the basket was set up in order to maintain the distance of 7.5 cm from a source of light.

2-3. Method for judging

The skins are observed after removal of the batch, and then the skins were abserved immediately after irradiation of light, after 24 hours and 48 hours.

The standard for judging the skin's reaction is similar to the case of 1-4.

2-4. Result

In the result of poisonous test by light on the healthy skin and the horny layer enfoliating skin in respect of respective products including cream, pack, milky lotion and beauty wash, at all events the deep red dapples were not recognized before irradiation of light, immediately after irradiation of light, after 24 hours and after 48 hours. Namely, it is considered that the primary irritations of skin based on the irradiation of light do not exist nearly.

Solcoseryl has very high moisture retaining ability as mentioned above, and also the hygroscopic ability of solcoseryl is equal to that of propylene glycol and glycerin.

(3) The test of moisture retaining ability and hygroscopic ability in solcoseryl 3-1. Experimental object and experimental method (i) Experimental object (a) solcoseryl (b) glycerin (c) propylene glycol After moistures being contained in the aforesaid respective samples are evaporated on the water bath, the substances which are dried at 105° C. for 4 hours were used for experimental samples.

(ii) Experimental method (a) A sample of about 1 g is weighed accurately in the weighing bottle having diameter of about 4.5 cm, and this sample was stood in the environmental condition including relative humidity of 58% and temperature of 20 C., and then the following experiments were carried out for the substances which reached a constant weight.

(b)

The moisture retaining ability test; 20° C. relative humidity 32%.

The hydroscopic ability test (1); 20° C. relative humidity 79%.

The hydroscopic ability test (2); 20° C. relative humidity 98%.

(c) The measuring times were regarded as 1, 3, 5, 7, 12 and 24 hours.

(d) The establishment of environmental conditions

The following aqueous solutions of saturated salt are placed in the desiccator and were stood in the thermostatic chamber having the temperature of 20° C.

| 20°C. relative humidity | saturated aqueous solution |
|---|---|
| 98% | lead (II) nitrate; Pb(NO$_3$)$_2$ |
| 79% | ammonium chloride; NH$_4$Cl |
| 58% | sodium bromide; NaBr.2H$_2$O |
| 32% | calcium chloride; CaCl$_2$.6H$_2$O |

3-2. Experimental result (1) Moisture retaining ability test;

The moisture retaining abilities (presented by decreasing rate of weight) under the condition including relative humidity of 32% and temperature of 20° C. are indicated in Table 1.

TABLE 1

| | variation of weight (%) | | | | | |
|---|---|---|---|---|---|---|
| | 1 hour | 3 hours | 5 hours | 7 hours | 12 hours | 24 hours |
| solcoseryl | −0.004 | −0.011 | −0.016 | −0.021 | −0.026 | −0.034 |
| glycerin | −0.003 | −0.013 | −0.025 | −0.036 | −0.064 | −0.084 |
| propylene glycol | −0.012 | −0.037 | −0.063 | −0.090 | −0.179 | −0.214 |

(2) Hygroscopic ability test (1);

The hygroscopic abilities (presented by increasing rate of weight) under the condition including relative humidity of 79% and temperature of 20° C. are indicated in Table 2.

TABLE 2

| | variation of weight (%) | | | | | |
|---|---|---|---|---|---|---|
| | 1 hour | 3 hours | 5 hours | 7 hours | 12 hours | 24 hours |
| solcoseryl | 0.034 | 0.080 | 0.117 | 0.151 | 0.486 | 0.740 |
| glycerin | 0.040 | 0.101 | 0.153 | 0.198 | 0.658 | 1.012 |
| propylene glycol | 0.038 | 0.091 | 0.136 | 0.177 | 0.695 | 1.080 |

(3) Hygroscopic ability test (2);

The hygroscopic abilities (presented by increasing rate of weight) under the condition including relative humidity of 98% and temperature of 20° C. are indicated in Table 3.

TABLE 3

| | variation of weight (%) | | | | | |
|---|---|---|---|---|---|---|
| | 1 hour | 3 hours | 5 hours | 7 hours | 12 hours | 24 hours |
| solcoseryl | 0.050 | 0.132 | 0.206 | 0.280 | 0.788 | 1.132 |
| glycerin | 0.093 | 0.203 | 0.318 | 0.407 | 0.896 | 1.262 |
| propylene glycol | 0.057 | 0.169 | 0.275 | 0.385 | 0.996 | 1.365 |

3-3. Conclusion

In order to understand from Table 1-3, this solcoseryl is slightly inferior to glycerin and propylene glycol in the hygroscopic ability, but said solcoseryl is nearly equal to them, and the solcoseryl is superior to the both in the moisture retaining ability.

(4) Moisture retaining ability of RAFFIPENET-010

Moisture retaining ability test based on the experiment of 3-1(ii) b for the samples prepared by same method as the experiment 3-1, in order to test the moisture retaining ability of RAFFINPENET-010;

The moisture retaining abilities (presented by decreasing rate of weight) of RAFFIPENET-010 were investigated under the condition including relative humidity of 32% and temperature of 20° C., and said moisture retaining abilities were compared with the decreasing rate of weight for solcoseryl under the same condition.

| | variation of weight (%) | | | | | |
|---|---|---|---|---|---|---|
| | 1 hour | 3 hours | 5 hours | 7 hours | 12 hours | 24 hours |
| solcoseryl | −0.004 | −0.011 | −0.016 | −0.021 | −0.026 | −0.036 |
| RAFFI-PENET-010 | −0.002 | −0.006 | −0.009 | −0.010 | −0.012 | −0.015 |

CONCLUSION

RAFFIPENET-010 is the substance that a matter which DNA is dissolved in the raffinose ester of higher fatty acid is added to solcoseryl further, and the moisture retaining ability of said RAFFIPENET-010 is improved in the range from 30 to 60% than the simple solcoseryl according to the experiment as mentioned above.

As mentioned above, the composition of the present invention is stable over wide range of pH for cosmetics, and also does not give the primary irritation of the skin, has no variable nature and has an excellent moisture retaining ability, and then can give the cosmetics which the feeling obtained by employing said cosmetics is very satisfactory.

What is claimed is:

1. A topical moisturizing composition comprising 0.1–4.0 weight % of a raffinose ester of higher fatty acid having 14 to 20 carbon atoms, 0.1–4.0 weight % of cane sugar fatty acid ester, and 3.0–5.0 weight % of a moisture-retaining solcoseryl, and a cosmetically acceptable carrier selected from the group consisting of water, squalene, octyldodecanol, lanolin, avocado oil, glycerine, ethanol and polyvinyl alcohol.

2. A topical cosmetic composition as claimed in claim 1, wherein the higher fatty acid ester of the raffinose ester is at least one member selected from the group consisting of myristic acid and stearic acid.

3. A topical moisturizing composition comprising 0.1–4.0 weight % of a raffinose ester of higher fatty acid having 14 to 20 carbon atoms, 0.1–4.0 weight % of cane sugar fatty acid ester and 3.0–5.0 weight % of a moisture-retaining solcoseryl.

4. A topical moisturizing composition comprising 0.1–4.0 weight % of a raffinose ester of higher fatty acid having 14 to 20 carbon atoms, 0.1 to 4.0 weight % of cane sugar fatty acid ester, 3.0–5.0 weight % of a moisture-retaining solcoseryl, and an effective amount of deoxyribonucleic acid for increasing moisture-retaining ability, and a cosmetically acceptable carrier selected from the group consisting of water, squalene, octyldodecanol, lanolin, avocado oil, glycerine, ethanol and polyvinyl alcohol, wherein the preparation of the composition includes the deoxyribonucleic acid being dissolved in the raffinose ester, which is added to the solcoseryl.

5. A topical cosmetic composition as claimed in claim 4, wherein the higher fatty acid of the raffinose ester is at least one member selected from the group consisting of myristic acid and stearic acid.

6. A topical moisturizing composition comprising 0.1–4.0 weight % of a raffinose ester of higher fatty acid having 14 to 20 carbon atoms, 0.1–4.0 weight % of cane sugar fatty acid ester, 3.0–5.0 weight % of a moisture-retaining solcoseryl, and an effective amount of deoxyribonucleic acid for increasing moisture-retaining ability, the composition being prepared by the steps of:

(a) dissolving the deoxyribonucleic acid into a portion of the raffinose ester, (b) adding the solcoseryl to the resulting formulation of step (a), (c) mixing the cane sugar fatty acid ester and the remaining portion of the raffinose ester together, and (d) mixing the formulations from step (b) and (c) together and compounding.

* * * * *